US006958241B2

(12) United States Patent
Martin et al.

(10) Patent No.: US 6,958,241 B2
(45) Date of Patent: *Oct. 25, 2005

(54) THERAPEUTIC LIPOSOME COMPOSITION AND METHOD

(76) Inventors: Francis J. Martin, 160 San Fernando Way, San Francisco, CA (US) 94127; Samuel Zalipsky, 1202 Truman St., Redwood City, CA (US) 94061; Shi Kun Huang, 18798 Madison Ave., Castro Valley, CA (US) 94546

(*) Notice: Subject to any disclaimer, the term of this patent is extended or adjusted under 35 U.S.C. 154(b) by 0 days.

This patent is subject to a terminal disclaimer.

(21) Appl. No.: 10/616,094

(22) Filed: Jul. 8, 2003

(65) Prior Publication Data

US 2004/0009217 A1 Jan. 15, 2004

Related U.S. Application Data

(63) Continuation of application No. 09/501,857, filed on Feb. 10, 2000, now Pat. No. 6,660,525, which is a continuation of application No. 08/949,039, filed on Oct. 10, 1997, now Pat. No. 6,043,094.
(60) Provisional application No. 60/027,923, filed on Oct. 11, 1996.

(51) Int. Cl.[7] .......................... C12N 15/88; C12N 5/06; C12N 5/12; A61K 9/127
(52) U.S. Cl. ...................... 435/458; 435/375; 424/450
(58) Field of Search ............................... 435/458, 375; 424/450

(56) References Cited

U.S. PATENT DOCUMENTS

| | | | |
|---|---|---|---|
| 4,935,465 A | | 6/1990 | Garman |
| 5,013,556 A | | 5/1991 | Woodle et al. |
| 6,043,094 A | * | 3/2000 | Martin et al. ............... 435/458 |
| 6,660,525 B2 | * | 12/2003 | Martin et al. ............... 435/458 |

FOREIGN PATENT DOCUMENTS

| | | |
|---|---|---|
| EP | 0 317 957 B1 | 5/1989 |
| EP | 0 526 700 B1 | 2/1993 |
| WO | WO 94/21281 A1 | 9/1994 |

OTHER PUBLICATIONS

Copy of International Search Report for PCT/US97/18813.
Allen et al., "A new strategy for attachment of antibodies to sterically stabilized liposomes resulting in efficient targeting to cancer cells", Biochimica et Biophysica Acta 1237 (1995); pp. 99–108.
Anwer et al., "Optimization of Cationic Lipid/DNA Complexes for Systemic Gene Transfer to Tumor Lesions", Journal of Drug Targeting vol. 8, No. 2 (2000); pp. 125–135.
Baldwin et al., "Effect on Polymyxin B on Experimental Shock from Meningococcal and Escherichia coli Endotoxins", The Journal of Infectious Diseases 164 (1991); pp. 542–549.

Blume et al., "Specific targeting with poly(ethylene glycol)–modified liposomes: coupling of homing devices to the ends of the polymeric chains combines effective target binding with long circulation times", Biochimica et Biophysica Acta 1149 (1993); pp. 180–184.
Bone, "The Pathogenesis of Sepsis", Annals of Internal Medicine 115 (1991); pp. 457–469.
Capon and Ward, "The CD4–gp120 Interaction and Aids Pathogenesis", Annual Review of Immunology 9 (1991); pp. 649–678.
Defrees et al., "Sialyl Lewis x Liposomes as a Multivalent Ligand and Inhibitor of E–Selectin Mediated Cellular Adhesion", Journal of the American Chemical Society 118 (1996); pp. 6101–6104.
Dinarello, "Interleukin–1 and Interleukin–1 Antagonism", Blood vol. 77, No. 8 (1991); pp. 1627–1652.
Friedmann, "Overcoming the Obstacles to Gene Therapy", Scientific American (1997); pp. 96–101.
Haynes, "Scientific and Social Issues of Human Immunodeficiency Virus Vaccine Development", Science 260 (1993); pp. 1279–1286.
Heath et al., "Covalent Attachment of Immunoglobulins to Liposomes Via Glycosphingolipids", Biochimica et Biophysica Acta 640 (1981); pp. 66–81.
Humphries et al., "A Synthetic Peptide from Fibronectin Inhibits Experimental Metastasis of Murine Melanoma Cells", Science 233 (1986); pp. 467–470.
Ichikawa et al., "Chemical–Enzymatic Synthesis and Conformational Analysis of Sialyt Lewis x and Derivatives", Journal of the American Chemical Society 114 (1992); pp. 9283–9298.
Kano et al., "The Activation of cAMP–Dependent Protein Kinase is Directly Linked to the Inhibition of Osteoblast Proliferation (UMR–106) by Parathyroid Hormone–Related Protein", Biochemical and Biophysical Research Communications vol. 174, No. 3 (1991); pp. 97–101.
Kawasaki et al., "Amino Acids and Peptides.XIV. Laminin Related Peptides and Their Inhibitory Effect on Experimental Metastasis Formation", Biochemical and Biophysical Research Communications vol. 174, No. 3 (1991); pp. 1159–1162.

(Continued)

Primary Examiner—James Ketter
Assistant Examiner—Konstantina Katcheves
(74) Attorney, Agent, or Firm—Michael Atkins (57) ABSTRACT

A method of liposome-based therapy for a mammalian subject is disclosed. The method uses liposomes with outer surfaces that contain an affinity moiety effective to bind specifically to a biological surface at which the therapy is aimed, and a hydrophilic polymer coating effective to shield the affinity moiety from interaction with the target surface. The hydrophilic polymer coating is made up of polymer chains covalently linked to surface lipid components in the liposomes through releasable linkages. After a desired liposome biodistribution is achieved, a releasing agent is administered to cause cleaving of a substantial portion of the releasable linkages in the liposomes, to expose the affinity agent to the target surface.

15 Claims, 6 Drawing Sheets

OTHER PUBLICATIONS

Kirpotin et al., "Liposomes with detachable polmer coating: destabilization and fusion of dioleoylphosphatidylethanolamine vesicles triggered by cleavage of surface–grafted poly-(ethylene glycol)", FEBS Letters 388 (1996); pp. 115–118.

Klibanov and Huang, "Long–Circulating Liposomes: Development and Perspectives", Journal of Liposome Research vol. 2, No. 3 (1992); pp. 321–334.

Martin et al., "Immunospecific Targeting of Liposomes to Cells: A Novel and Efficient Method for Covalent Attachment of Fab' Fragments via Disulfide Bonds", Biochemistry 20 (1981); pp. 4229–4238.

Martin and Papahadjopoulos, "Irreversible Coupling of Immunoglobulin Fragments to Preformed Vesicles", Journal of Biological Chemistry vol. 257, No. 1 (1982); pp. 286–288.

Martin, "Pharmaceutical Manufacturing of Liposomes", Chapter 6, Specialized Drug Delivery Systems: Manufacturing and Production Technology (Marcel Dekker, Inc, New York and Basel) (1990); pp. 267–316.

Phillips et al., "ELAM–1 Mediates Cell Adhesion by Recognition of a Carbohydrate Ligand, Sialyi–Le", Science 250 (1990); pp. 1130–1132.

Robbins and Ghivizzani, "Viral Vectors for Gene Therapy", Pharmacology & Therapeutics vol. 80, No. 1 (1998); pp. 35–47.

Schofield and Caskey, "Non–viral approaches to gene therapy", British Medical Bulletin vol. 51, No. 1 (1995); pp. 56–71.

Stylianou et al., "Interleukin 1 Induces NF–KB through Its Type I but Not Its Type II Receptor in Lymphocytes", Journal of Biological Chemistry vol. 267, No. 22 (1992); pp. 15836–15841.

Szoka, "Comparative Properties and Methods of Preparation of Lipid Vesicles (Liposomes)", Annual Review of Biophysics and Bioengineering 9 (1980); pp. 467–508.

Uster et al., "Insertion of poly(ethylene glycol) derivatized phospholipid into pre–formed liposomes results in prolonged in vivo circulation time", FEBS Letters 386 (1996); pp. 243–246.

Waldmann, "Immune Receptors: Targets for Therapy of Leukemia/Lymphoma, Autoimmune Diseases and for the Prevention of Allograft Rejection", Annual Review of Immunology 10 (1992); pp. 675–704.

Yuan et al., "Vascular Permeability in a Human Tumor Xenograft: Molecular Size Dependence and Cutoff Size", Cancer Research 55 (1995); pp. 3752–3756.

Zalipsky and Lee, "Use of Functionalized Poly(Ethylene Glycol)s for Modification of Polypeptides", Chapter 21, Poly(Ethylene Glycol) Chemistry: Biotechnical and Biomedical Applications (J. Milton Harris. Plenum Press, New York) (1992); pp. 347–370.

Zalipsky et al., "Evaluation of a New Reagent for Covalent Attachment of Polyethylene Glycol to Proteins", Biotechnology and Applied Biochemistry 15 (1992); pp. 100–114.

Zalipsky, "Synthesis of an End–Group Functionalized Polyethylene Glycol–Lipid Conjugate for Preparation of Polymer–Grafted Liposomes", Bioconjugate Chemistry 4 (1993); pp. 296–299.

Zalipsky et al., "Long circulating, cationic liposomes containing amino–PEG–phosphatidylethanolamine", FEBS Letters 353 (1994); pp. 71–74.

Zalipsky, "Polyethylene Glycol–Lipid Conjugates", Chapter 9, Stealth Liposomes (CRC Press) (1995); pp. 93–102.

* cited by examiner

THERAPEUTIC LIPOSOME COMPOSITION AND METHOD

This application is a continuation of U.S. application Ser. No. 09/501,857, filed Feb. 10, 2000, now U.S. Pat. No. 6,660,525, which is a continuation of U.S. application Ser. No. 08/949,039, filed Oct. 10, 1997, now U.S. Pat. No. 6,043,094, both of which claims the benefit of U.S. provisional application No. 60/027,923, filed Oct. 11, 1996, all of which are incorporated herein by reference in their entirety.

FIELD OF THE INVENTION

The present invention relates to a therapeutic composition and method that employs, as the delivery vehicle, liposomes having an affinity moiety on the outer liposome surfaces. The moiety is shielded by a surface coating of hydrophilic polymers, until the liposomes contact a releasing agent effective to remove the surface coating.

REFERENCES

Abbas, A. K., et al., in *CELLULAR AND MOLECULAR IMMUNOLOGY* (W. B. Saunders Company Harcourt Brace Jovanovich, Philadelphia, Pa.) (1991).

Allen, T. M., et al., *Biochemicia et Biophysica Acta* 1237:99–108 (1995).

Baldwin, G., et al., *J. Infect. Diseas.* 164:542–549 (1991).

Blume, G., et al., *Biochimica et Biophysica Acta, Biomembranes* 1149:180–184 (1993).

Borman, S., *Chem. Eng. News* 7:25–28 (1992).

Capon, D. J., and Ward, R. H. R., *Ann. Rev. Immunol.* 9:649–678 (1991).

DeFrees, S. A., et al., *J. Am. Chem. Soc.* 118:6101–6104 (1996).

Dinarello, C. A., *Blood* 77(8):1627–1650 (1991).

Heath, T. D., *Biochem. et Biophys. Acta,* 640:66 (1981).

Humphries, M. J., et al., *Science* 233:467–469 (1986).

Ichikawa, Y., et al., *J. Am. Chem. Soc.* 114:9283–9298 (1992).

Jawetz, E., in *BASIC AND CLINICAL PHARMACOLOGY* (Katzung, B. G., Ed.) Apple & Lange, Los Altos, Calif., pg. 511 (198-7).

Kawasaki, K., et al., *Biochem. Biophys. Res. Comm.,* 174(3):1159–1162 (1991).

Kano, J., et al., *Biochem. Biophys. Res. Comm.* 179:97–101 (1991).

Kirpotin, D., et al., *FEBS Letters* 388:115–118 (1996).

Klibanov, A. L., et al., *Journal of Liposome Research* 2 (3):321–334 (1992).

Maniatis, T., et al., in *MOLECULAR CLONING: A LABORATORY MANUAL* (Cold Spring Harbor Laboratory Press, Cold Spring Harbor, N.Y.) (1989).

Martin, F. J., *Biochemistry* 20:4229 (1981).

Martin, F. J., *J. Biol Chem.* 257:286 (1982).

Martin, F. J, in *SPECIALIZED DRUG DELIVERY SYSTEMS-MANUFACTURING AND PRODUCTION TECHNOLOGY,* (P. Tyle, Ed.) (Marcel Dekker, New York) pp. 267–316 (1990).

Phillips, M. L., et al., *Science* 250:1130–1132 (1990).

Stylianou, E., et al., *J. Biol. Chem.* 267:15836–15841 (1992).

Szoka, F., Jr., et al., *Ann. Rev. Biophys. Bioeng.* 9:467 (1980).

Uster, P. S., et al., *FEBS Letters* 386:243:246 (1996).

Waldmann, T. A., *Annu. Rev. Immunol.* 10:675–704 (1992).

Woodle, U.S. Pat. No. 5,013,556, issued May 7, 1991.

Yuan, F., et al., *Cancer Res.,* 55:3752–3756 (1995).

Zalipsky, S., et al., in *POLY(ETHYLENE GLYCOL) CHEMISTRY: BIOTECHNICAL AND BIOMEDICAL APPLICATIONS* (J. M. Harris, Ed.) Plenum Press, pg. 347–370 (1992a).

Zalipsky, S., et al., *Biotechnol. Appl. Biochem.* 15:100 (1992b).

Zalipsky, S., *Bioconjugate Chemistry* 4(4):296–299 (1993).

Zalipsky, S., et al., *FEBS Letters* 353:71–74 (1994).

Zalipsky, S., in *STEALTH LIPOSOMES* Chapter 9 (D. Lasic and F. Martin, Eds.) CRC Press, Boca Raton, Fla., (1995).

BACKGROUND OF THE INVENTION

Liposomes are used for a variety of therapeutic purposes, in particular, for carrying therapeutic agents to target cells by systemic administration of liposomes.

When liposomes are administered systemically, it is desirable to coat the liposomes with a hydrophilic agent, for example, a coating of hydrophilic polymer chains such as polyethylene glycol, to extend the blood circulation lifetime of the liposomes. An extended circulation time is often needed for liposomes to reach the target region, cell or site from the site of injection.

The use of such long-circulating liposomes, that is, liposomes with a surface coating of hydrophilic polymer chains, such as polyethylene glycol (PEG) chains, for targeting has been proposed (Allen, et al., 1995; DeFrees, et al., 1996; Blume, et al., 1993; Klibanov, et al., 1992; Woodle, 1991; Zalipsky, 1993; Zalipsky, 1994; Zalipsky, 1995). In one approach, a ligand, such as an antibody, for targeting the liposomes is linked to the polar head group of lipids forming the liposome. The problem with this approach is that the ligand is covered by the PEG chains, interfering with the ligand's interaction with the target and reducing its effectiveness as a targeting agent.

In another approach, the targeting ligand is attached to the distal ends of the PEG chains forming the hydrophilic polymer coating (Klibanov, et al., 1992; Kirpotin, et al., 1992). While this approach improves targeting, since the targeting moiety is more exposed, the approach has drawbacks in that the PEG chains act to stabilize liposome, making release of the liposome's contents at the target site difficult and in that the attached moiety can compromise the extended blood circulation lifetime provided by the surface coating of hydrophilic polymer chains (Klibanov, et al., 1992).

For a variety of reasons, it may be desirable to shield all or at least a portion of the targeting moieties attached to the liposome until a desired biodistribution of the liposomes is achieved. If a high density of moieties is desired, and all of the targeting moieties in an exposed state on liposome surface, the presence of the moieties may limit the blood circulation time of the liposomes. Another problem with unshielded targeting moieties is that the moiety may direct liposomes to non-target surfaces or cells, before a desired biodistribution is reached.

Therefore, it is desirable to provide a therapeutic liposome composition including affinity moieties, e.g., targeting moieties, where all or at least a portion of the moieties are initially shielded from interaction with a target surface, but which can be unshielded when a desired biodistribution is reached.

SUMMARY OF THE INVENTION

In one aspect, the invention includes a method of liposome-based therapy for a mammalian subject which includes systemically administering to the subject, liposomes with outer surfaces that contain (i) an affinity moiety effective to bind specifically to a target surface at which the therapy is aimed, and (ii) a hydrophilic polymer coating effective to shield the affinity moiety from interaction with the target surface. The hydrophilic polymer coating is made up of polymer chains which are covalently linked to surface lipid components in the liposomes through releasable linkages. The administered liposomes are allowed to circulate systemically until a desired biodistribution of the liposomes is achieved, and a releasing agent is then administered to the subject in an amount effective to cause release of a substantial portion of the releasable linkages in the administered liposomes, thereby to expose the affinity agent to the target surface.

In one embodiment of the method, the releasable linkages are reducible chemical linkages such as disulfide, ester or peptide linkages. In a preferred embodiment, the releasable linkages are disulfide linkages and the releasing agent is cysteine, glutathione or ascorbate.

In another embodiment, the releasable linkages are pH sensitive linkages, heat sensitive linkages or light sensitive linkages.

The hydrophilic polymer forming the liposome surface coating is selected from the group consisting of polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, and polyaspartamide.

In a preferred embodiment, the hydrophilic polymer chains are polyethylene glycol chains having molecular weights in the range 500 to 10,000 daltons.

In one embodiment, where a therapeutic agent is to be administered to a target region, the affinity moiety is a ligand effective to bind specifically with a receptor at the target region, and the liposomes include the therapeutic agent in entrapped form.

An example of this embodiment is treatment of a solid tumor, where the affinity moiety is effective to bind specifically to a tumor-specific antigen, the liposomes have an average size between 30–400 nm and include an entrapped drug, and the releasing agent is administered to the subject after the liposomes have extravasated into the tumor.

In another embodiment, the method of the invention is for treatment at a site of inflammation, wherein the affinity moiety is effective to bind specifically to infected cells, the liposomes have an average size between 30–400 nm and carry an entrapped therapeutic agent, and the releasing agent is administered after the liposomes have extravasated at the site of inflammation.

In another embodiment, the affinity moiety is a polypeptide or polysaccharide effector molecule capable of inhibiting a pathogenic cell-binding event, that is, binding between a first binding member, such as a pathogen or cell in the bloodstream, and a second binding member, such as a target cell or cell matrix. Preferably, the molecule is one of the following:

(a) a CD4 glycoprotein, for use in treating the subject for infection by human immunodeficiency virus (HIV);

(b) a polysaccharide which binds to endothelial leukocyte adhesion molecule (ELAM), for use in treating inflammation related to neutrophil recruitment and tissue infiltration;

(c) polymyxin B or polymyxin B decapeptide, for treating the subject for septic shock; or (d) a peptide.

In a preferred embodiment, the method is for use in treating the subject for septic shock, and the affinity moiety is polymyxin B.

In another aspect, the invention includes a liposome composition for use in treating a subject with an affinity moiety which is capable of inhibiting binding between a first binding member, which is a pathogen or cell in the bloodstream, and a second binding member, which is a target cell or cell matrix. The liposomes have outer surfaces that contain (i) a hydrophilic polymer coating composed of polymer chains that are covalently linked to surface lipid components in the liposomes through releasable linkages, and (ii) the affinity moiety bound to the outer surfaces of the liposomes, such that the affinity moiety is shielded by said hydrophilic polymer coating from interaction with such binding members and is exposed for interaction with such binding members when the hydrophilic polymer coating is released.

These and other objects and features of the invention will be more fully appreciated when the following detailed description of the invention is read in conjunction with the accompanying drawings.

BRIEF DESCRIPTION OF THE DRAWINGS

FIG. 3 illustrates a vesicle-forming lipid derivatized with polyethyleneglycol through a peptide linkage (FIG. 3A), an ester linkage (FIG. 3B) and a disulfide linkage (FIG. 3C);

DETAILED DESCRIPTION OF THE INVENTION

I. Liposome Composition

Figure 1:
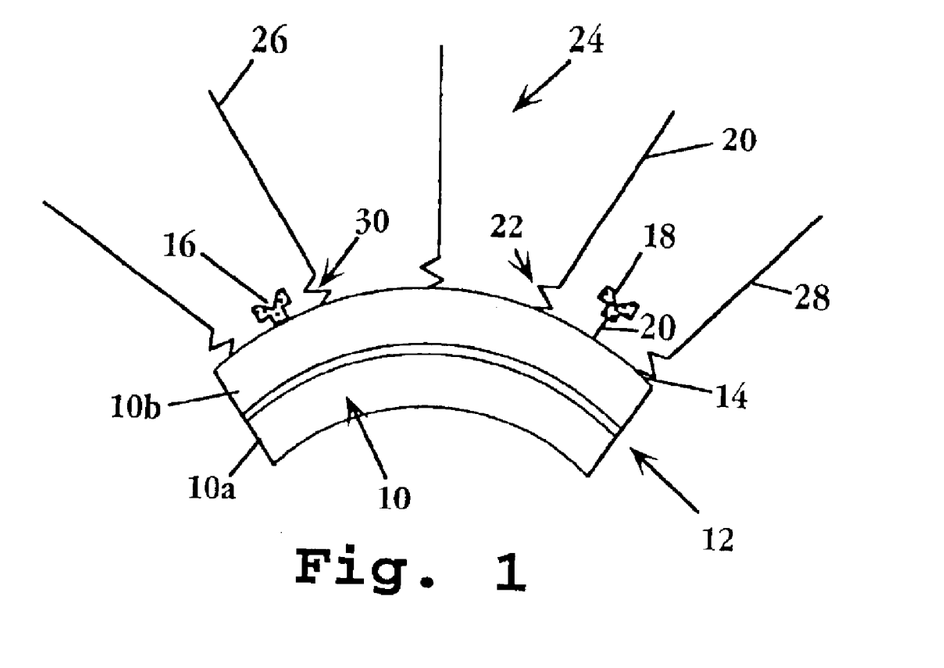
FIG. 1 illustrates a liposome of the present invention having a surface coating of releasable hydrophilic polymer chains and affinity moieties.

A liposome for use in liposome-based therapy, in accordance with the present invention, is illustrated in FIG. 1. The figure shows a portion of the outer bilayer 10 of a liposome 12 having an outer surface 14. It will be appreciated that the liposome may include additional bilayers and that for simplicity only the outer bilayer is shown.

The outer bilayer is composed of confronting lipid layers 10a and 10b which are the interior and exterior lipid layers, respectively, of the bilayer, each layer being composed of vesicle-forming lipids, such as phospholipids and cholesterol, typically having a diacyl hydrophobic lipid tail and a polar head group. Liposome 12 is composed primarily of such vesicle-forming lipids, and exemplary lipids are given below.

The outer surface of liposome 12 contains affinity moieties, such as moiety 16, effective to bind specifically to a target, e.g., a biological surface such as a cell membrane, a cell matrix, a tissue or target surface or region at which the liposome-based therapy is aimed. The affinity moiety is bound to the outer liposome surface by covalent attachment to surface lipid components in the liposomes, as will be described. In a preferred embodiment, the moiety is bound directly to surface lipid components by covalent attachment to the head group of a vesicle-forming lipid. Alternatively, the ligand is bound to the liposome by attachment to a liposome lipid through a short polymer chain, such as moiety 18 attached via chain 20. Alternatively, or in addition, an affinity moiety is attached to a distal end of a releasable hydrophilic polymer chain.

The affinity moiety, as will be described below, is a ligand effective to bind specifically and with high affinity to ligand-binding molecules carried on the target. For example, in one embodiment, the affinity moiety is effective to bind to a tumor-specific antigen in a solid tumor and in another embodiment, the affinity moiety is effective to bind to cells at a site of inflammation. In another embodiment, the affinity moiety is a polypeptide or polysaccharide effector molecule effective to inhibit a cell-binding event, that is, to interfere with binding between a first binding member and a second binding member. These and other embodiments of suitable moieties are described below.

With continuing reference to FIG. 1, liposome 12 has an outer surface coating 24 of hydrophilic polymer chains, such as chains 26, 28, which are preferably densely packed to form a brushlike coating effective to shield liposome surface components. According to an important feature of the invention, the hydrophilic polymer chains are connected to the liposome lipids by chemically releasable bonds, such as linkage 30 on chain 26. The releasable bond is typically a covalent chemical bond that can be released by a suitable cleaving agent, such as a reducing agent, a reduced or elevated pH, a hydrolytic enzyme, a change in temperature, or a photolytic stimulus, as described further below. Exemplary hydrophilic polymers and releasable linkages are described below.

According to an important feature of the invention, the hydrophilic surface coating is effective to shield the affinity moiety from interaction with its target, that is, the biological surface to which the affinity moiety binds. When the hydrophilic polymer coating is released, as will be described, the affinity moiety is exposed for interaction with its target.

In one embodiment of the invention, a therapeutic agent to be administered to a target cell or region is entrapped in liposome 12. As used herein, therapeutic agent, compound and drug are used interchangeably. The compound may be entrapped in the inner aqueous compartment of the liposome or in the lipid bilayer, depending on the nature of the compound. Exemplary compounds are described below.

A. Vesicle-Forming Lipid Component

The liposome composition of the present invention is composed primarily of vesicle-forming lipids. Such a vesicle-forming lipid is one which (a) can form spontaneously into bilayer vesicles in water, as exemplified by the phospholipids, or (b) is stably incorporated into lipid bilayers, with its hydrophobic moiety in contact with the interior, hydrophobic region of the bilayer membrane, and its head group moiety oriented toward the exterior, polar surface of the membrane.

The vesicle-forming lipids of this type are preferably ones having two hydrocarbon chains, typically acyl chains, and a head group, either polar or nonpolar. There are a variety of synthetic vesicle-forming lipids and naturally-occurring vesicle-forming lipids, including the phospholipids, such as phosphatidylcholine, phosphatidylethanolamine, phosphatidic acid, phosphatidylinositol, and sphingomyelin, where the two hydrocarbon chains are typically between about 14–22 carbon atoms in length, and have varying degrees of unsaturation. The above-described lipids and phospholipids whose acyl chains have varying degrees of saturation can be obtained commercially or prepared according to published methods. Other suitable lipids include glycolipids and sterols such as cholesterol.

Preferred diacyl-chain lipids for use in the present invention include diacyl glycerol, phosphatidyl ethanolamine (PE) and phosphatidylglycerol (PG). These lipids are preferred for use as the vesicle-forming lipid, the major liposome component, and for use in the derivatized lipid described below.

Additionally, the vesicle-forming lipid is selected to achieve a specified degree of fluidity or rigidity, to control the stability of the liposome in serum and to control the rate of release of the entrapped agent in the liposome. The rigidity of the liposome, as determined by the vesicle-forming lipid, may also play a role in fusion of the liposome to a target cell, as will be described.

Liposomes having a more rigid lipid bilayer, or a liquid crystalline bilayer, are achieved by incorporation of a relatively rigid lipid, e.g., a lipid having a relatively high phase transition temperature, e.g., up to 60° C. Rigid, i.e., saturated, lipids contribute to greater membrane rigidity in the lipid bilayer. Other lipid components, such as cholesterol, are also known to contribute to membrane rigidity in lipid bilayer structures.

On the other hand, lipid fluidity is achieved by incorporation of a relatively fluid lipid, typically one having a lipid phase with a relatively low liquid to liquid-crystalline phase transition temperature, e.g., at or below room temperature.

The lipids forming the bilayer vesicle, i.e., liposome, can also be cationic lipids, which have a lipophilic moiety, such as a sterol, an acyl or diacyl chain, and where the lipid has an overall net positive charge. Preferably, the head group of the lipid carries the positive charge. Exemplary cationic lipids include 1,2-dioleyloxy-3-(trimethylamino)propane (DOTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethylammonium bromide (DORIE); N-[1-(2,3-dioleyloxy)propyl]-N,N,N-trimethylammonium chloride (DOTMA); 3β[N-(N',N'-dimethylaminoethane)carbamoly]cholesterol (DC-Chol); and dimethyldioctadecylammonium (DDAB).

The cationic vesicle-forming lipid may also be a neutral lipid, such as dioleoylphosphatidyl ethanolamine (DOPE) or an amphipathic lipid, such as a phospholipid, derivatized with a cationic lipid, such as polylysine or other polyamine lipids. For example, the neutral lipid (DOPE) can be derivatized with polylysine to form a cationic lipid.

B. Hydrophilic Polymer Coating

As described above, the liposomes of the invention contain a hydrophilic polymer coating made up of polymer chains which are linked to liposome surface lipid components through releasable linkages. Such hydrophilic polymer chains are incorporated in the liposome by including between about 1–20 mole percent of a releasably linked, hydrophilic polymer-lipid conjugate, prepared as described below.

Hydrophilic polymers suitable for use in the polymer coating include polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, and polyaspartamide.

In a preferred embodiment, the hydrophilic polymer is polyethyleneglycol (PEG), preferably as a PEG chain having a molecular weight between 500–10,000 daltons, more preferably between 2,000–10,000 daltons and most preferably between 1,000–5,000 daltons.

The surface coating on the liposome provided by the hydrophilic polymer chains provides colloidal stability and serves to protect the liposomes from uptake by the reticuloendothelial system, providing a long blood circulation lifetime for the liposomes to distribute in the organism. The extent of enhancement of blood circulation time is preferably severalfold over that achieved in the absence of the polymer coating, as described in co-owned U.S. Pat. No. 5,013,556.

The hydrophilic polymer chains also shield the surface-bound affinity moieties, masking the affinity moieties from interaction with the target until the liposomes have distributed in the subject. The affinity moieties are exposed by releasing the cleavable linkage between the lipid and the hydrophilic polymer chain. Exposure of the affinity moieties allows interaction with the target to promote site-specific delivery of the liposome and/or its contents or to inhibit a cell-binding event, as will be described.

In studies performed in support of the invention, described below, liposomes having a releasable coating of PEG chains were prepared and administered in vivo. A releasing agent was injected after liposome administration to cleave the bond attaching the PEG chains to the liposome, releasing the hydrophilic chains, and achieving retention of the liposomes in specific tissue regions.

C. Releasable Linkage

As described above, the liposomes of the present invention include an outer surface coating of hydrophilic polymer chains which are attached to the liposome through a releasable linkage.

In one embodiment, the releasable linkage is a chemically releasable linkage which is cleaved by administration of a suitable releasing agent or under selective physiological conditions, such as in the presence of enzymes or reducing agents. For example, ester and peptide linkages are cleaved by esterase or peptidase enzymes. Disulfide linkages are cleaved by administration of a reducing agent, such as glutathione or ascorbate, or by a reducing agent present in vivo, such as cysteine, which is present in plasma and intracellularly.

Other releasable linkages include pH sensitive bonds and bonds which are cleaved upon exposure to glucose, light or heat.

For example, the hydrophilic polymer chains are attached to the liposome by a pH sensitive bond, and the liposomes are targeted to a site having a pH effective to cleave the bond and release the hydrophilic chains, such as a tumor region. Exemplary pH sensitive bonds include acyloxyalkyl ether, acetal and ketal bonds.

Figure 2:
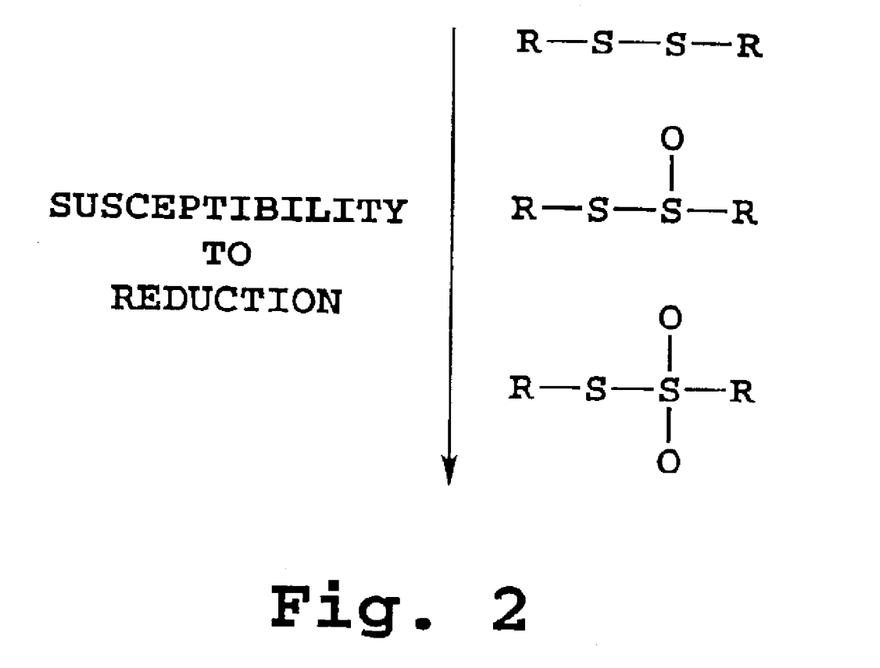
FIG. 2 shows several disulfide linkages and their relative susceptibility to cleavage by a nucleophile.

In a preferred embodiment, the cleavable bond is a disulfide bond, broadly intended herein to refer to sulfur-containing bonds, such as those shown in FIG. 2. The sulfur-containing bonds are synthesized to achieve a selected degree of lability, as indicated in the figure, and include a disulfide bond, a mixed sulfide-sulfone bond and a sulfide-sulfoxide bond. Of the three bonds, the disulfide bond is least susceptible to thiolysis and the sulfide-sulfoxide bond is most susceptible.

Such bonds are useful to tailor the rate of release of the hydrophilic polymer segment from the liposome surface. For example, a very labile disulfide bond is preferred for liposome targeting to blood cells or endothelial cells, since these cells are readily accessible and a shorter liposome blood circulation lifetime is needed. At the other extreme, a long-lasting or hearty disulfide bond is preferred when the liposomal target is tumor tissue, sites of inflammation or infection, skin or other organs, and peripheral lymphatic tissues. In these cases, a longer liposome blood circulation lifetime is generally needed for the liposomes to reach the desired target.

The releasable bond attaching the hydrophilic polymer chains to the liposome is cleaved in vivo typically as a result of change in environment, such as when the liposomes reach a specific site with a slightly lower pH, such as a region of tumor tissue, or a site with reducing conditions, such as a hypoxic tumor. Reducing conditions in vivo can also be effected by administration of a reducing agent, such as ascorbate, cysteine or glutathione. The cleavable bond may also be broken in response to an external stimuli, such as light or heat.

In studies performed in support of the present invention, described below, liposomes having a releasable surface coating of polyethylene glycol were prepared, where the polyethylene glycol chains were attached to the liposome by a labile, disulfide bond. The liposomes were administered to mice and allowed to distribute. A reducing agent was administered to effect release of the polymer chains. Tissue analysis of the mice lung and liver indicated that the hydrophilic polymer coating was released, as evidenced by retention of the liposomes in these organs.

D. Affinity Moiety

The affinity moiety in the liposome composition is generally effective to bind specifically to a target, that is, a biological surface such as a target cell surface or membrane, a cell matrix, a region of plaque, or the like. The affinity moieties are bound to the liposome surface by direct attachment to a liposomal lipid or by attachment through a short polymer chain, as will be described.

In one embodiment, the affinity moiety is a ligand effective to bind specifically with a receptor at the target region, more specifically, a ligand for binding to a receptor on a target cell. Non-limiting examples of ligands suitable for this purpose are listed in Table 1.

TABLE 1

LIGAND-RECEPTOR PAIRS AND ASSOCIATED TARGET CELL

| LIGAND | RECEPTOR | CELL TYPE |
| --- | --- | --- |
| folate | folate receptor | epithelial carcinomas, bone marrow stem cells |
| water soluble vitamins | vitamin receptor | various cells |
| pyridoxyl phosphate | CD4 | CD4 + lymphocytes |
| apolipoproteins | LDL | liver hepatocytes, vascular endothelial cells |
| insulin | insulin receptor | |
| transferrin | transferrin receptor | endothelial cells (brain) |

TABLE 1-continued

LIGAND-RECEPTOR PAIRS AND ASSOCIATED TARGET CELL

| LIGAND | RECEPTOR | CELL TYPE |
|---|---|---|
| galactose | asialoglycoprotein receptor | liver hepatocytes |
| sialyl-Lewis$^x$ | E, P selectin | activated endothelial cells |
| Mac-1 | L selectin | neutrophils, leukocytes |
| VEGF | Flk-1,2 | tumor epithelial cells |
| basic FGF | FGF receptor | tumor epithelial cells |
| EGF | EGF receptor | epithelial cells |
| VCAM-1 | $\alpha_4\beta_1$ integrin | vascular endothelial cells |
| ICAM-1 | $\alpha_L\beta_2$ integrin | vascular endothelial cells |
| PECAM-1/CD31 | $\alpha_v\beta_3$ integrin | vascular endothelial cells |
| fibronectin | $\alpha_v\beta_3$ integrin | activated platelets |
| osteopontin | $\alpha_v\beta_1$ and $\alpha_v\beta_5$ integrins | endothelial cells and smooth muscle cells in atherosclerotic plaques |
| RGD sequences of matrix proteins | $\alpha_v\beta_3$ integrin | tumor endothelial cells, vascular smooth muscle cells |
| HIV GP 120/41 or GP120 C4 domain peptomers | CD4 | CD4 + lymphocytes |
| HIV/GP 120/41 (T cell tropic isolates) or SDF-1 chemokines | fusin | CD4 + lymphocytes |
| HIV GP120/41 (Macro-phage tropic isolates) | Chemokine receptor CC-CRK-5 | macrophages, dendritic cells |
| Anti-cell surface receptor antibodies (or fragments thereof) | cell surface receptors | erythrocytes, platelets |
| Anti-cell surface receptor antibodies (or fragments thereof) | cell surface receptors such as CD-34 | bone marrow stem cells |

The ligands listed in Table 1 are used, in one embodiment of the invention, to target the liposomes, after release of the hydrophilic surface coating, to specific target cells. For example, a folate ligand attached to the head group of DSPE or to the distal end of a short PEG chain derivatized to DSPE can be incorporated into the liposomes. A "short" PEG chain, as used herein is meant to specify a PEG chain having a length (molecular weight) selected such that the ligand, when incorporated into the liposome, is masked or shielded by the surface coating of hydrophilic polymer chains, as illustrated in FIG. 1. A surface-bound folate ligand incorporated into the liposome is effective to bind to folate receptors on epithelial cells for administration of an entrapped therapeutic agent to the target cell, for example, administration of a neoplastic agent for treatment of epithelial carcinomas.

Another example of affinity moieties suitable for use in the method and composition of the present invention include cytokines, such as those listed in Table 2. The therapeutic uses of such cytokines have been described in the literature (Abbas, et al., 1991) and include treatment of medical conditions which respond to indirect therapy of stimulation of the body's natural immune response. Such conditions include immunodeficiency diseases, such as AIDS, chronic infections and certain types of cancers. Some cytokine effectors may be administered on a short term basis to enhance a weak immunogenic or weak microbicidal response. The effectors may be administered on a long term basis as part of a therapy treatment for cancer or AIDS (Waldmann, 1992). Such cytokines are obtained by recombinant production methods, according to published procedures, and are typically administered in an amount to achieve an effective cytokine concentration of about 0.1–1 micromolar in the bloodstream.

TABLE 2

| CYTOKINE | POLYPEPTIDE SIZE |
|---|---|
| A. Mediators of Natural Immunity | |
| IFN-alpha | 18 kD (monomer) |
| IFN-beta | 20 kD (monomer) |
| Tumor necrosis factor (TNF) | 17 kD (homotrimer) |
| Interleukin-1 (alpha and beta) | 17 kD (monomer) |
| Interleukin-6 | 26 kD (monomer) |
| Interleukin-8's | 8–10 (monomer or dimer) |
| B. Mediators of Lymphocyte Activation, Growth and Differentiation | |
| Interleukin-2 | 14–17 kD (monomer) |
| Interleukin-4 | 20 kD (monomer) |
| Transforming growth factor (beta) | 14 kD (monomer or dimer) |
| C. Mediators of Effector Cell Adhesion | |
| Gamma Interferon | 21–24 kD (homodimer) |
| Lymphotoxin | 24 kD (homotrimer) |
| Interleukin-5 | 20 kD (monomer) |
| D. Mediators of Immature Leukocyte Growth and Differentiation | |
| Interleukin-3 | 20–26 kD (monomer) |
| Granulocyte-macrophage Colony Stimulating Factor | 22 kD (monomer) |
| Macrophage Colony stimulating Factor | 40 kD (dimer) |
| Granulocyte CSF | 19 kD (monomer) |
| Interleukin-7 | 25 kD (monomer) |

The affinity moiety can also be an inhibitor of IL-1 activity, where the moiety is an IL-1 inhibitor, or IL-1 receptor antagonist (IL1RA), which blocks binding of IL-1 to receptors on lymphocyte cell surfaces (Stylianou, et al., 1992).

IL-1 production is stimulated, by both endotoxins which cause septic shock and exotoxins which cause toxic shock syndrome (Dinarello, 1991). IL-1 production during septic shock or toxic shock may exacerbate the clinical symptoms observed in patients. Therefore, use of an IL-1 inhibitor affinity moiety to decrease the clinical symptoms associated with either toxic shock or septic shock may be beneficial.

IL-1 inhibitor is a 52 to 66 Kd polypeptide that binds specifically to IL-1 to inhibit its immunostimulatory responses. IL1RA is a 23 to 25 KD polypeptide that competes with binding of IL-1 to its cell surface receptors to inhibit IL-1's immunostimulatory responses.

Another example of an affinity moiety contemplated for use in the present invention is a peptide hormone, for example, parathyroid hormone. Parathyroid hormone is 84 amino acids in length and can inhibit osteoblast division. Certain bone cancers are characterized by uncontrolled osteoblast division (Kano, et al., 1991) and administration of the hormone may be beneficial in such a condition. The affinity moiety as a peptide hormone can also be used to target the liposome to a cell that contains receptors for a specific peptide hormone.

In one preferred embodiment of the invention, the affinity moiety is a polypeptide or polysaccharide effector molecule effective to inhibit a cell-binding event. That is, the affinity moiety is capable of inhibiting binding between a first binding member and a second binding member. Typically, such an affinity moiety is effective as a pharmacological agent when circulating in free form in the bloodstream, but is rapidly removed from the bloodstream by renal clearance, typically within 1–2 hours. Exemplary effectors include CD4 glycoprotein, a polysaccharide, such as sialyl-Lewis$^x$, for inhibiting binding of neutrophils to ELAM-1, polymyxin B and a peptide sequence, such as YIGSR or RGDS. These examples are described below.

1. CD4 Glycoprotein. Numerous therapies for the prevention and treatment of human immunodeficiency virus (HIV) infection and acquired immune deficiency syndrome (AIDS) have been proposed. These therapies target different steps in the process of viral infection. Frequently, therapy includes the administration of drugs which interfere with viral replication, such as AZT and DDI. The administration of these drugs is accompanied by toxic side effects, since the replication process of normal cells is also affected.

Another step in the process of viral infection which is targeted in therapy is viral attachment to cells. HIV binds with specificity to the CD4 receptor of CD4+ T cells. By mechanisms not yet fully understood, the CD4+ cells eventually can become infected by HIV. Soluble CD4 receptor polypeptides have been administered intravenously to HIV-infected patients to prevent further HIV infection of a patient's CD4+ T cell population. Heretofore, this therapy has not been effective, since CD4 receptor fragments are rapidly cleared from circulation in the blood stream, and inhibitory plasma concentrations cannot be maintained (Capon and Ward, 1991).

The effector molecule in this embodiment is a soluble CD4 receptor polypeptide capable of binding to the gp120 glycoprotein of human immunodeficiency virus (HIV) to prevent binding of HIV to CD4+ T cells. The effector can be produced according to known recombinant methods (Maniatis, et al., 1989). In a preferred embodiment covalent attachment of CD4 is accomplished by coupling periodate oxidized CD4 with a polymer chain activated with a hydrazide group.

CD4 administered as a liposomal composition will remain in the bloodstream for a longer period of time. The CD4 effector composition can be administered intravenously during early or late stages of HIV infection, most beneficially in combination with other drugs used in AIDS therapeutics, so that HIV particles bound to the liposomes, to the extent these are taken up by infected cells, will also deliver a dose of the anti-viral agent to the infected cells. AZT and DDI are examples of anti-HIV drugs which may be encapsulated in the liposome compositions.

The liposome composition should be administered intravenously in a dose equivalent to an effective blood stream CD4 concentration of 1–10 micromolar. Doses of 5–40 mg CD4/kg body weight can be administered, typically at intervals of 2–14 days between treatments, with the level of HIV present in the bloodstream being monitored during treatment by standard assay methods.

Principal advantages of this composition are the increased circulation time of the CD4 effector in the blood stream and the polyvalent presentation of the effector on the surface of the liposomes, after the hydrophilic polymer chains have been released. Improved affinities of polyvalent CD4 presentation has recently been described (Chen, et al.). As described above, CD4 receptor fragments are cleared rapidly by renal filtration. Covalent attachment of the CD4 polypeptide to liposomal carriers prevents renal clearance, and permits circulation of the polypeptide effector composition for 24–48 hours in the blood stream.

Additionally, the polyvalent CD4-bearing liposomes resemble CD4+ T cell lymphocytes in that the CD4 glycoproteins are presented on hydrophobic surfaces which mimic the surfaces of T cell lymphocytes. This presentation is likely to serve as a decoy binding HIV particles and HIV infected cells expressing gp120 so that healthy CD4+ lymphocytes are spared.

2. Polysaccharide Effector Inflammation causes the expression of a polypeptide, endothelial leukocyte adhesion molecule-1 (ELAM-1), on the surface of endothelial cells of blood vessels, adjacent to sites of inflammation. ELAM-1, in turn, recognizes and binds a polysaccharide moiety, sialyl-Lewis$^x$, on surfaces of neutrophils and leukocytes and recruits such cells to sites of inflammation. By preventing the recognition and binding of neutrophils by ELAM-1, excessive inflammatory responses due to conditions such as reperfusion injury, septic shock, and chronic inflammatory diseases, can be avoided.

In this embodiment, the affinity moiety is the tetrasaccharide, sialyl-Lewis$^x$, recognized by ELAM-1 (Phillips, et al., 1990), for therapeutic use in preventing excessive recruitment of neutrophils to sites of inflammation in the bloodstream. Sialyl-Lewis$^x$ is produced by the glycosylation mutants of Chinese hamster ovary (CHO) cells, and may be obtained in purified form from the cultured cells (Phillips, et al., 1990). Alternatively, the affinity moiety is produced by chemical and/or enzymatic synthesis (Borman, 1992; Ichikawa, et al., 1992). Preparation of sialyl-Lewisx-PEG-DSPE conjugate has been described (DeFrees, et al., 1996).

3. Polymyxin B. In this embodiment, the effector is a compound which is useful in the prevention and treatment of septic shock. The causal agents of septic shock are endotoxins which accumulate during systemic gram-negative bacterial infections (Jawetz, 1987). Because of the rapid onset of severe sepsis, treatment is often not begun until critical stages of sepsis.

The antimicrobial agent which has been used most successfully in treating septic shock against in cases of septic shock is polymyxin B. Polymyxin B reacts with and neutralizes gram-negative bacterial endotoxins, specifically *E. coli* 0111:B4 liposaccharide (LPS) (Baldwin, et al., 1991). Polymyxin B can be chemically synthesized or isolated from spore-forming gram-positive bacilli, such as *Bacillus polymyxa*. Because the compound is rapidly excreted, high doses of polymyxin B are required for effective treatment. The high doses can lead to severe renal toxicity.

In the present invention, polymyxin B is attached to the liposomes by the coupling methods described herein. Administration of polymyxin B attached to liposomes will extend its blood circulation lifetime. The affinity moiety is initially shielded by the liposome-attached hydrophilic polymer chains, and exposed after distribution by administering a releasing agent.

Such a liposomal composition is administered on a short term basis, at a polymyxin B dose of 0.1–0.5 mg/kg body weight, as a prophylactic for individuals at risk of, or suffering from acute septic shock.

4. Peptide In this embodiment, the affinity moiety is a short peptide that has cell-binding activity and is effective to compete with a ligand for a receptor site. Inhibition of the ligand-receptor cell-binding event results in arresting an infection process.

In general, useful peptides will have cell-binding activity due to a portion of sequence other than the end of the peptide. In this way, after attachment to the polymer chain on the liposome, the peptide remains active. Another general feature of useful peptides is their small size. Peptides of between about 4–20 amino acids are preferred.

One exemplary peptide, YIGSR, is useful for blocking metastases of tumors (Kawasaki, et al., 1991). YIGSR is one of the peptide sequences in the B1 chain of laminin responsible for the glycoprotein's adhesive properties and is known to bind to the laminin receptor. Laminin, the protein in which the YIGSR sequence occurs, is a constituent of basement membranes. Circulating metastatic cells which overexpress the laminin receptor may find their way to laminin molecules in the basement membrane where they may become attached and establish metastatic tumors. By introducing exogenous YIGSR, the laminin receptors of circulating metastatic cells are blocked, thereby inhibiting tumor establishment.

Similarly, the peptide arginine-glycine-aspartic acid-serine (RGDS) has experimentally been shown to inhibit the establishment of metastatic tumors by interfering with the binding of tumor cells to fibronectin (Humphries, et al., 1986). Like YIGSR, RGDS is a peptide sequence involved with tumor cell adhesion to basement membranes.

Such a peptide can be obtained from natural sources or can be an synthesized from organic sources to generate a peptide mimic.

E. Therapeutic Agent

In one embodiment of the invention, the liposomes are for use in administering a therapeutic agent a target and include a therapeutic agent entrapped within the liposome.

The entrapped therapeutic agent may be any of a large number of therapeutic agents that can be entrapped in lipid vesicles, including water-soluble agents that can be stably encapsulated in the aqueous compartment of the vesicles, lipophilic compounds that stably partition in the lipid phase of the vesicles, or agents that can be stably attached, e.g., by electrostatic attachment to the outer vesicle surfaces. Exemplary water-soluble compounds include small, water-soluble organic compounds, peptides, proteins, DNA plasmids, oligonucleotides and gene fragments.

In a preferred embodiment of the invention, the liposomes contain an entrapped drug for treatment of a solid tumor, such as doxorubicin, daunomycin or vincristine.

The entrapped agent may also be a reporter molecule, such as an enzyme or a fluorophore, for use in in vitro diagnostic assays. Such liposomes having an entrapped reporter molecule may be delivered by fusion to either target cells or receptor-containing liposomes.

Lipid vesicles containing the entrapped agent are prepared according to well-known methods, such as those described above, typically, hydration of a lipid film, reverse-phase evaporation, and solvent infusion. The compound to be delivered is either included in the lipid film, in the case of a lipophilic compound, or is included in the hydration medium, in the case of a water-soluble therapeutic agent. Alternatively, the therapeutic agent may be loaded into preformed vesicles, e.g., by loading an ionizable compound. against a pH gradient.

II. Liposome Preparation

A. Preparation of Releasable Polymer Coating

The hydrophilic polymer chains are attached to the liposome through a releasable linkage, that is, a linkage that cleaves in response to a selected stimulus.

Figure 3A:
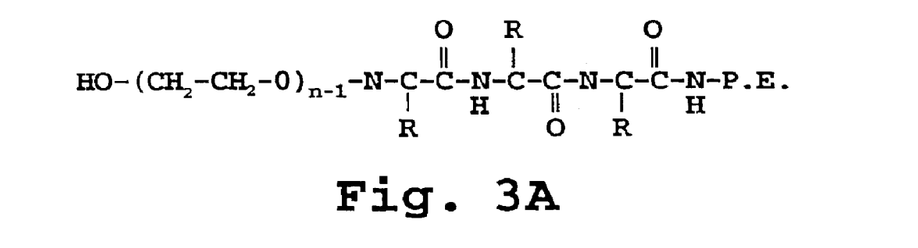
Figure 3B:
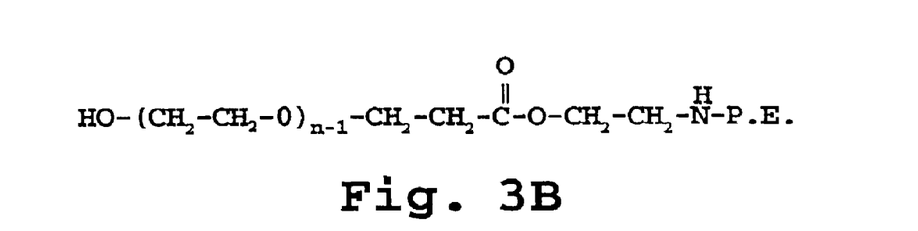
Figure 3C:
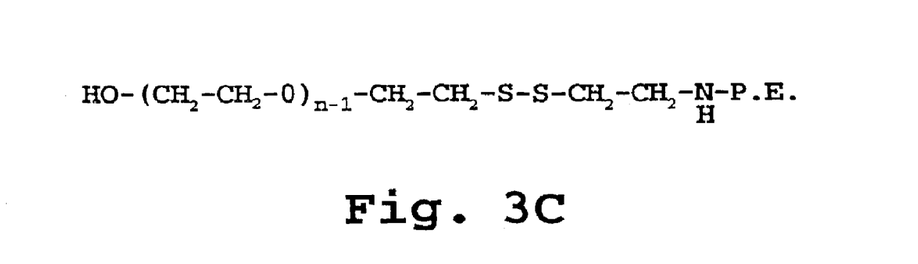

In one embodiment, the releasable linkage is a peptide, ester or disulfide linkage, and FIG. 3 shows exemplary lipids which are linked through peptide (FIG. 3A), ester (FIG. 3B) and disulfide (FIG. 3C) containing linkages.

Figure 4:
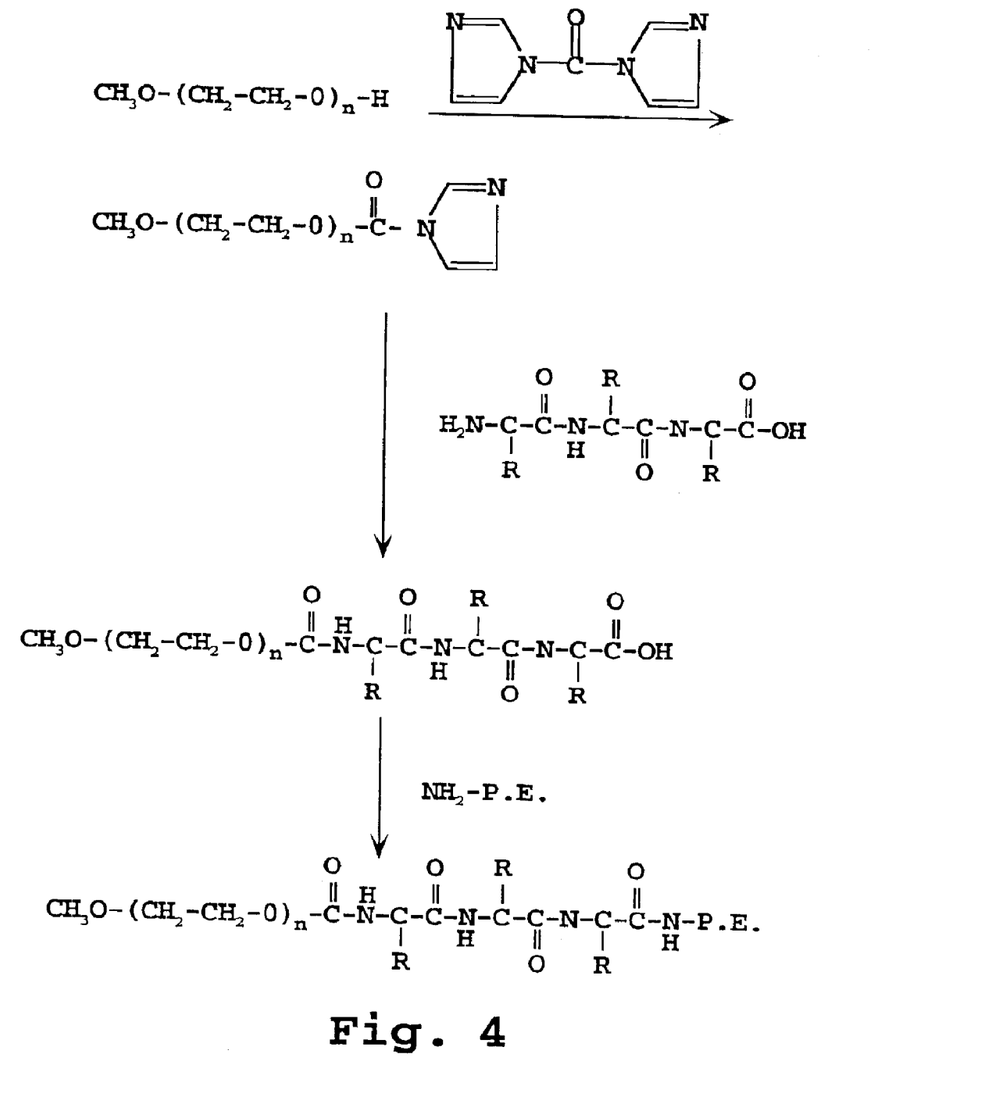
FIG. 4 illustrates a reaction scheme for preparing phosphatidylethanolamine (PE) derivatized with polyethyleneglycol through a releasable peptide linkage.

A peptide-linked compound is prepared, for example, by coupling a polyalkylether, such as PEG, to a lipid amine, as illustrated in FIG. 4. End-capped PEG is activated with a carbonyl diimidazole coupling reagent, to form the activated imidazole compound shown in FIG. 4. The activated PEG is then coupled to with the N-terminal amine of the exemplary tripeptide shown. The peptide carboxyl group can then be used to couple a lipid amine group, through a conventional carbodiimide coupling reagent, such as dicyclohexylcarbodiimide (DCC).

The ester linked compound (FIG. 3B) can be prepared, for example, by coupling a lipid acid, such as phosphatidic acid, to the terminal alcohol group of a polyalkylether, using alcohol via an anhydride coupling agent. Alternatively, a short linkage fragment containing an internal ester bond and suitable end groups, such as primary amine groups, can be used to couple the polyalkylether to the vesicle-forming lipid through amide or carbamate linkages.

Figure 5:
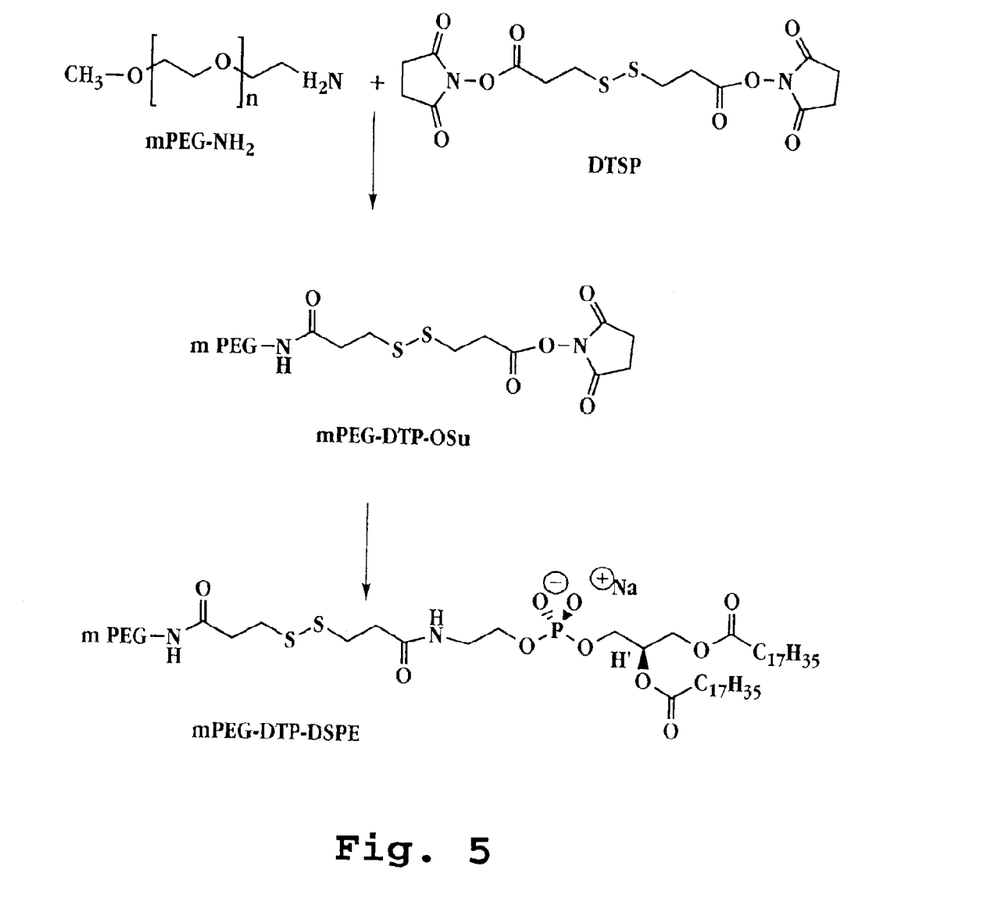
FIG. 5 illustrates a reaction scheme for preparing PE derivatized with polyethyleneglycol through a releasable disulfide linkage.

In a preferred embodiment, the releasable linkage is a disulfide linkage, prepared as described in Example 1 and illustrated in FIG. 5. As detailed in Example 1A, an intermediate mPEG-DTP-OSu is prepared by reacting methoxypoly(ethylene glycol)amine with an excess of dithiobis(succinimidyl propionate) (DTSP) dissolved in dimethyl formamide (DMF). Under these conditions, the desired product, mPEG-DTP-OSu, constituted the bulk of the polymer recovered from the reaction mixture (70–80% by NMR). The minor product, symmetrical disulfide of N-(mPEG)-mercaptopropionamide, did not interfere with the DSPE-coupling reaction. The recovered polymer was reacted with DSPE until the latter was completely consumed. The conjugate, mPEG-DTP-DSPE, was purified by removing the excess of PEG-reagents by dialysis. Thiolytic lability of the conjugate was confirmed by its incubation with an excess of DTT resulting in the disappearance of the original spot (Rf=0.55) on TLC, and the appearance of two new spots (Rf=0.68 and 0.23 for PEG and lipid components, respectively).

In another embodiment, the releasable linkage is a pH sensitive linkage, a light sensitive linkage or a heat sensitive linkage.

pH sensitive bonds are preferably one which are cleared in response to low pH target regions in the body, for example, such areas of localized acidity are found in tumors. Exemplary pH sensitive bonds include acyloxyalkyl ether, acetal and ketal bonds.

Light sensitive linkages are those that cleave upon irradiation with an appropriate wavelength of light (ultraviolet light). For example, bonds that undergo a trans to cis isomerization on exposure to irradiation may be suitable. Alternatively, the liposome may incorporate a photosensitizing agent that absorbs light and alters a linkage in such a way to effect cleavage. In clinical use, the target treatment site, such as a neoplasm, would be irradiated by a suitable light source, such as an endoscope having a diffuser tip attached to the fiberoptic bundle. A laser, such as a aluminum/gallium/arsenic laser can be used to illuminate a target, particularly a small tumor or micrometastisis. Other suitable illumination sources include filtered tungsten, xenon or mercury light sources, and pump lasers.

B. Attachment of Affinity Moiety

As described above, the liposomes of the present invention contain an affinity moiety attached to the surface of the PEG-coated liposomes. The affinity moiety is attached to the liposomes by direct attachment to liposome lipid surface components or through a short spacer arm or tether, depending on the nature of the moiety.

A variety of methods are available for attaching molecules, e.g., affinity moieties, to the surface of lipid vesicles. In one preferred method, the affinity moiety is coupled to the lipid, by a coupling reaction described below, to form an affinity moiety-lipid conjugate. This conjugate is added to a solution of lipids for formation of liposomes, as will be described. In another method, a vesicle-forming lipid activated for covalent attachment of an affinity moiety is incorporated into liposomes. The formed liposomes are exposed to the affinity moiety to achieve attachment of the affinity moiety to the activated lipids.

A variety of methods are available for preparing a conjugate composed of an affinity moiety and a vesicle-forming lipid. For example, water-soluble, amine-containing affinity moieties can be covalently attached to lipids, such as phosphatidylethanolamine, by reacting the amine-containing moiety with a lipid which has been derivatized to contain an activated ester of N-hydroxysuccinimide.

As another example, biomolecules, and in particular large biomolecules such as proteins, can be coupled to lipids according to reported methods. One method involves Schiff-base formation between an aldehyde group on a lipid, typically a phospholipid, and a primary amino acid on the affinity moiety. The aldehyde group is preferably formed by periodate oxidation of the lipid. The coupling reaction, after removal of the oxidant, is carried out in the presence of a reducing agent, such as dithiotreitol, as described by Heath (1981). Typical aldehyde-lipid precursors suitable in the method include lactosylceramide, trihexosylceramine, galacto cerebroside, phosphatidylglycerol, phosphatidylinositol and gangliosides.

A second general coupling method is applicable to thiol-containing affinity moieties, and involves formation of a disulfide or thioether bond between a lipid and the affinity moiety. In the disulfide reaction, a lipid amine, such as phosphatidylethanolamine, is modified to contain a pyridylditho derivative which can react with an exposed thiol group in the affinity moiety. Reaction conditions for such a method can be found in Martin (1981). The thioether coupling method, described by Martin (1982), is carried out by forming a sulfhydryl-reactive phospholipid, such as [N-(4)P-maleimido-phenyl(butyryl) phosphatidylethanolamine], and reacting the lipid with the thiol-containing affinity moiety.

Another method for reacting an affinity moiety with a lipid involves reacting the affinity moiety with a lipid which has been derivatized to contain an activated ester of N-hydroxysuccinimide. The reaction is typically carried out in the presence of a mild detergent, such as deoxycholate. Like the reactions described above, this coupling reaction is preferably performed prior to incorporating the lipid into the liposome.

The above-described coupling techniques are exemplary and it will be appreciated that other suitable methods are known in the art and have been described, for example in U.S. Pat. Nos. 6,605,630, 4,731,324, 4,429,008, 4,622,294 and 4,483,929.

Methods for attachment of an affinity moiety to the liposome through a short spacer arm have been described, such as in U.S. Pat. No. 4,762,915. In general, attachment of a moiety to a spacer arm can be accomplished by derivatizing the vesicle-forming lipid, typically DSPE, with a hydrophilic polymer, such as PEG, having a reactive terminal group for attachment of an affinity moiety. Methods for attachment of ligands to activated PEG chains are described in the art (Allen, et al., 1995; Zalipsky, 1993; Zalipsky, 1994; Zalipsky, 1995a; Zalipsky, 1995b). In these methods, the inert terminal methoxy group of mPEG is replaced with a reactive functionality suitable for conjugation reactions, such as an amino or hydrazide group. The end functionalized PEG is attached to a lipid, typically DSPE. The functionalized PEG-DSPE derivatives are employed in liposome formation and the desired ligand is attached to the reactive end of the PEG chain before or after liposome formation.

As a specific example, attachment of the ligand sialyl-Lewisx to a PEG-DSPE conjugate has been described (DeFrees, et al., 1996).

C. Liposome Preparation

The liposomes may be prepared by a variety of techniques, such as those detailed in Szoka, et al., 1980. Multilamellar vesicles (MLVs) can be formed by simple lipid-film hydration techniques. In this procedure, a mixture of liposome-forming lipids of the type detailed above dissolved in a suitable organic solvent is evaporated in a vessel to form a thin film, which is then covered by an aqueous medium. The lipid film hydrates to form MLVs, typically with sizes between. about 0.1 to 10 microns.

The lipid components used in forming the fusogenic liposomes of the present invention are preferably present in a molar ratio of about 70–90 percent vesicle-forming lipids, 1–20 percent of a lipid derivatized with a releasable hydrophilic polymer chain, and 0.1–5 percent of a lipid having an attached affinity moiety. One exemplary formulation includes 80–90 mole percent phosphatidylethanolamine, 1–20 mole percent of PEG-DTP-DSPE, and 0.1–5 mole percent of affinity moiety-DSPE. Cholesterol may be included in the formulation at between about 1–50 mole percent. Preparation of an exemplary liposome formulation is described in Example 2.

Another procedure suitable for preparation of the fusogenic liposomes of the present invention is described by Uster, et al., 1996. In this method, liposomes with an entrapped therapeutic agent are prepared from vesicle-forming lipids. The preformed liposomes are added to a solution containing a concentrated dispersion of micelles of affinity moiety-DSPE conjugates and/or PEG-derivatized lipid conjugates and incubated under conditions effective to achieve insertion of the micellular lipid conjugates into the preformed liposomes.

Still another liposome preparation procedure suitable for preparation of the liposomes of the present invention is a solvent injection method. In this procedure, a mixture of the lipids, dissolved in a solvent, preferably ethanol or DMSO, is injected into an aqueous medium with stirring to form liposomes. The solvent is removed by a suitable technique, such as dialysis, and the liposomes are then sized as desired. This method achieves relatively high encapsulation efficiencies.

A hydrophilic therapeutic agent is entrapped in the liposomes by including the agent in the aqueous hydration mixture. A hydrophobic therapeutic agent is entrapped in the liposomes by including the agent with the lipids prior to formation of a thin film or dissolved in a lipid solvent prior to injection into an aqueous medium.

The liposomes are preferably prepared to have substantially homogeneous sizes in a selected size range, typically between about 0.03 to 0.5 microns. One effective sizing method for REVs and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less (Martin, 1990)

III. Method of Treatment

The invention includes, in one aspect, a method of liposome-based therapy for a mammalian subject which includes systemically administering to the subject, e.g., intravenously administering, liposomes having a surface-bound affinity moiety and a hydrophilic polymer coating. The hydrophilic polymer coating, composed of releasably attached polymer chains, is effective to shield the affinity moiety from interaction with its target. The administered liposomes are allowed to circulate systemically until a desired biodistribution of the liposomes is achieved. A releasing agent, as described above, is administered to the subject in an amount effective to cause cleaving of a substantial portion, e.g., greater than about 50%, more preferably greater than about 70%, of the releasable linkages in the administered liposomes. The affinity moiety is exposed upon release of the hydrophilic polymer chains for interaction with its target.

In a preferred embodiment, the liposomes are used for treatment of a solid tumor. The liposomes include an anti-tumor drug in entrapped form and are targeted to the tumor region by an affinity moiety effective to bind specifically to a tumor-specific antigen. For example, liposomes can be targeted to the vascular endothelial cells of tumors by including a VEGF ligand in the liposome, for selective attachment to Flk-1, 2 receptors expressed on the proliferating tumor endothelial cells.

In this embodiment, the liposomes are sized to between about 30–400 nm. Liposomes in this size range have been shown to be able to enter tumors through "gaps" present in the endothelial cell lining of tumor vasculature (Yuan, et al., 1995).

After administration of the liposomes, e.g., intravenous administration, and after sufficient time has elapsed to allow the liposomes to distribute through the subject and extravasate into the tumor, a releasing agent is administered to the subject to release the hydrophilic surface coating from the liposomes. Release of the surface coating is effective to expose the affinity moiety to effect binding of the liposomes to the target cells. In one embodiment, the hydrophilic surface coating is attached to the liposomes by a pH sensitive linkage, and the linkages are released after the liposomes have extravasated into the tumor, due to the hypoxic nature of the tumor region.

In another embodiment, the liposomes are for treatment at a site of inflammation. The liposomes include an affinity moiety effective to bind specifically to infected cells at the region, such as sialyl-Lewis$^x$.

The liposome composition, in a preferred embodiment, is used to competitively block cell binding events. Here the affinity moiety attached to the liposome surface is effective to interfere with binding between a first binding member, such as a pathogen or cell in the blood, and a second binding member, which is a target cell or cell matrix. In the examples given above, the affinity moiety is soluble CD4 glycoprotein, for inhibition of binding of HIV to CD4+ T cells; or is sialyl-Lewis$^x$ for inhibition of binding of neutrophils to ELAM-1 expressing cells at sites of inflammation; or is polymyxin B, for inhibition of binding of lipopolysaccharide to its target to arrest sepsis; or is a peptide such as YIGSR to bind to circulating metastasis and prevent their binding to cell matrices. The liposome composition is administered and allowed to distribute. An agent effective to release the hydrophilic polymer chains is brought into contact with the liposomes, either systemically via intravenous injection or locally via placement with catheter or other means, to expose the affinity moiety to its target. In this way, specific administration of a compound and/or blocking of a cell-binding event is a specific region is achieved.

The liposomes in any of the treatment methods described above, may include an entrapped therapeutic agent. The liposomes are administered and allowed to distribute, after which a releasing agent is administered to release the hydrophilic surface coating to expose the attached affinity moiety and initiate binding. In this way, the entrapped therapeutic compound is specifically and locally administered to the target.

A. In Vivo Administration

In studies performed in support of the invention, liposomes having a releasable coating of PEG were prepared and administered to mice, as described in Example 1. The releasable coating of PEG was formed by including in the liposomes PEG attached to DSPE through a thiolytically cleavable disulfide linkage (PEG-DTP-DSPE), prepared according to the scheme shown in FIG. 5.

As described in Example 3, complexes containing cationic liposomes with the releasable coating of PEG chains and a luciferase-bearing plasmid were prepared. The complexes were prepared by forming a cationic liposome-condensed plasmid complex and incubating the complex with micelles of PEG-DTP-DSPE or with micelles of PEG-DSPE, where the PEG is attached to DSPE by a conventional, e.g., non-cleavable, bond (Zalipsky, et al. 1992). The micelles of PEG-DSPE and PEG-DTP-DSPE insert into the cationic liposomes with incubation at room temperature and gentle vortexing for 5 minutes.

Three liposome formulations were prepared, as described in Example 3. In the first formulation, the PEG coating was not releasable, that is, the PEG was included in the liposomes as PEG irreversibly attached to DSPE. In the second formulation, the liposomes had a PEG surface coating where half of the PEG chains were releasably attached to the liposome surface, and the other half were not releasably attached. In the third formulation, the PEG surface coating on the liposomes was releasable. These formulations are indicated in FIGS. 6A–6B as "PEG", "PEG+R-PEG" and "R-PEG", respectively.

The liposome complexes were administered intravenously to mice. Five minutes after administration, the reducing agent cysteine was added to reduce the disulfide bonds, thereby releasing the releasable PEG from the liposomes. 24 hours after injection, the lung and the liver were analyzed for luciferase activity.

Figure 6A:
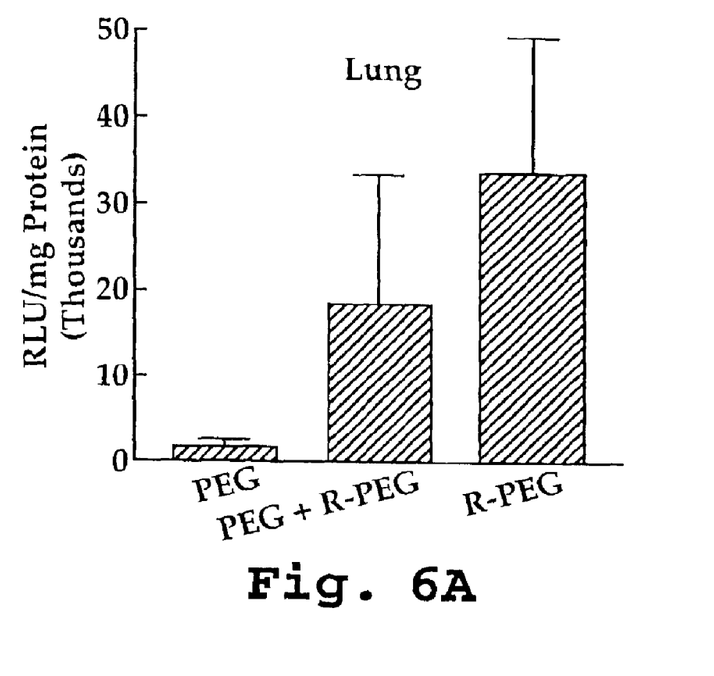
FIGS. 6A–6B are plots of relative luciferase units (RLU) per mg protein in the lung (FIG. 6A) and the liver (FIG. 6B) after in vivo administration to mice of liposome/plasmid complexes, where the liposomes have an outer surface coating of polyethyleneglycol by including in the liposome 2.5 mole percent of PEG covalently attached to DSPE ("PEG"), 1 mole percent of PEG covalently attached to DSPE and 1 mole percent of PEG attached to DSPE by a releasable bond ("PEG+R-PEG") or 2.5 mole percent of PEG attached to DSPE by a releasable bond ("R-PEG").
Figure 6B:
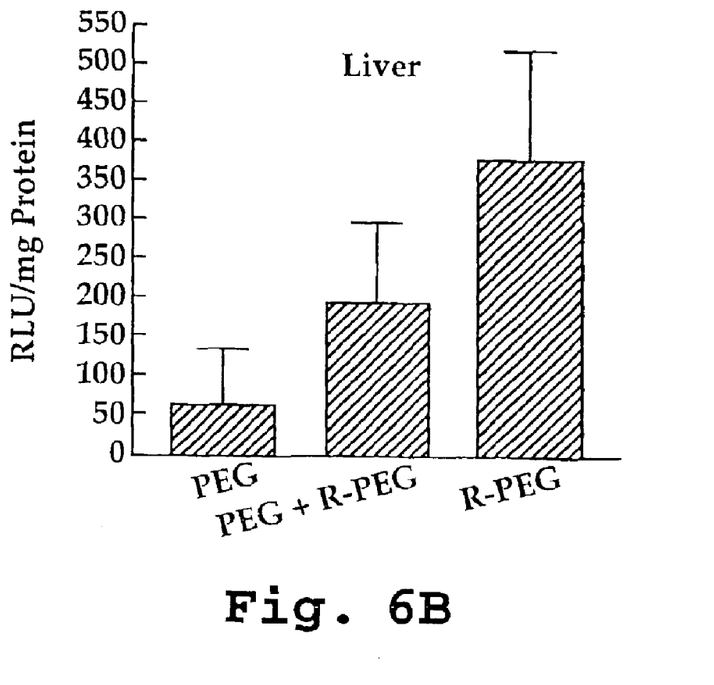

FIGS. 6A–6B, show that luciferase activity is higher, e.g., more liposomes are retained in the tissue, for liposomes which have releasable PEG chains. Importantly, the data demonstrates in vivo release of PEG chains by reduction of a releasable linkage. Release of the PEG chains exposes the positive liposome surface charges of the cationic liposomes, enhancing binding to the negative cell membranes and improving retention of the liposomes in the tissues, as evidenced by the higher luciferase activity for the releasable-PEG liposomal formulations.

B. Biodistribution Study

The PEG-coated cationic liposomes described above were prepared with Texas-red label to study the biodistribution of the liposomes after administration. A dose of cationic liposomes having a releasable surface coating of PEG chains was administered via tail vein injection to a mouse fitted with a transparent access chamber on a dorsal skin fold. Immediately after injection, a fluorescence micrograph was taken and shows that the liposomes enter the bloodstream for distribution through the subject, and remain in circulation for times sufficient for the liposomes to distribute to the skin vasculature. In contrast, cationic liposomes without the surface coating of PEG are not able to distribute effectively to reach the skin vasculature due to a short blood circulation halflife.

From the foregoing, it can be appreciated how various features and objects of the invention are met. The liposomes of the present invention provide a method for targeting liposomes, where the targeting moiety is shielded by a surface coating of releasable hydrophilic polymer chains. The hydrophilic surface coating reduces uptake of the liposomes, achieving a long blood circulation lifetime for distribution of the liposomes. After distribution, the hydrophilic surface coating is released from the liposomes, exposing the liposome-attached affinity moieties for multi-valent presentation and binding with the target.

IV. Examples

The following examples illustrate methods of preparing, characterizing, and using the liposomes of the present invention. The examples are in no way intended to limit the scope of the invention.

Example 1

Preparation of mPEG-DTP-DSPE

A. Preparation of N-succinimidyl-(2-(ωmethoxy-poly-(oxyethylene)-α-aminocarbonyl)ethyl-diothiopropionoate Intermediate, (mPEG-DTP-OSu)

This synthetic scheme is illustrated in FIG. 3. N-succinimidyl-(2-(ω-methoxypoly(oxyethylene)-α-aminocarbonyl)ethyl-diothiopropionoate (compound III), is prepared according to the method of Kirpotin, et al., 1996.

A solution of dithiobis(succinimidyl propionate) (873 mg, 2 mmol) (DTSP, compound II), prepared from dithiodipropionic acid (Aldrich, Milwaukee, Wis.), is dissolved in dimethylformamide (10 ml) and treated with methoxypoly (ethylene glycol)amine (2 g, 1 mmol), mPEG-NH$_2$ (compound I), prepared according to the method of Zalipsky (1983), and triethylamine (140 ml). The resulting N-succinimidyl ester polymer intermediate, N-succinimidyl-(2-(ω-methoxypoly(oxyethylene)-α-aminocarbonyl)ethyl-diothiopropionate (mPEG-DTP-OSu, compound III) is then purified by recrystallization twice from isopropanol, followed by drying in vacuo over phosphorus pentoxide, to remove residual water. The intermediate is characterized by $^1$H NMR, using deuterated methanol as solvent. $^1$H-NMR (CD$_3$OD): δ2.6 (m, SCH$_2$CH$_2$CON), 2,85 (s, Su, 4H), 3.0 (overlapping m, SCH$_2$CH$_2$CO$_2$-Su and SCH$_2$CH$_2$CON), 3.38 (s, CH$_3$, #h), 3.64 (s, PEG, ≈180H). The composition of the product mixture, i.e., the relative amount of mono-PEG-ylated (mPEG-DTP-OSu) to di-PEG-ylated dithiodipropanoate product (mPEG)$_2$DTP, is determined by comparing the relative integrations of peaks at 2.6 ppm and 2.85 ppm downfield from TMS, assigned to the desired succinate, versus a resonance at 3.0 ppm, assigned to (mPEG)$_2$DTP.

B. Lipid Attachment mPEG-DTP-OSu is prepared as described above in Example 1A and dissolved in CHCl$_3$. Solid DSPE (100 mg) was added to the CHCl$_3$ solution of the recovered polymer (600 mg) and triethylamine (240 μl). The suspension was incubated at 45° C. until it clarified. Complete consumption was confirmed by TLC. The polymer lipid conjugate (mPEG-DTP-DSPE) was purified by dialysis. Yield 269 mg (70%).

Example 2

Liposome Preparation

Liposomes are prepared according to standard procedures by dissolving in chloroform the following lipids: 85 mole percent distearyl phosphatidylglycerol (DSPG), 10 mole percent of the disulfide-linked PEG-DSPE conjugate prepared as described in Example 1, 1 mole percent of an affinity moiety-DSPE conjugate, and 4 mole percent cholesterol. The lipids are dried as a thin film by rotation under reduced pressure. The lipid film is hydrated by addition of an aqueous phase to form liposomes which are sized by sonication or by sequential extrusion through Nucleopore polycarbonate membranes with pore sizes of 0.4 μm, 0.2 μm, 0.1 μm and 0.5 μm to obtain liposomes of 100–150 nm in size.

Example 3

In Vivo Administration of Releasable PEG Liposomes

A. Liposome Formulations

Cationic liposomes having a surface coating of PEG and complexed to a luciferase-bearing plasmid were prepared as follows.

B. Preparation of Cationic Liposome/Plasmid Complex

Cationic liposomes composed of the lipids dimethyldioctadecylammonium and cholesterol (DDAB:CHOL) were prepared according to standard procedures by dissolving 10 μmole DDAB and 10 μmole CHOL in an organic solvent containing primarily CHCl$_3$. The lipid solution was dried as a thin film by rotation under reduced pressure. The lipid film was hydrated by the addition of the desired aqueous phase, e.g., water, saline or buffer, to form liposomes (at a total lipid concentration of 20 μmole/ml) which were sized by sonication or by sequential extrusion through Nucleopore polycarbonate membranes with pore sizes of 0.4 μm, 0.2 μm, 0.1 μm and 0.05 μm to obtain liposomes of 100–150 nm in size.

A luciferase plasmid was used as a report gene. The plasmid was condensed for complexing with the cationic liposomes by adding 100 μl of a solution containing 1 mg/ml total histone in an aqueous medium to 400 μl of solubilized plasmid (1 mg plasmid/ml). The condensed plasmid had an average diameter of approximately 150 nm, as measured by dynamic light scattering.

Cationic liposome/condensed plasmid complexes were prepared by adding 280 μl of the cationic liposome suspension (20 μmole/ml) to 500 μl of the histone-condensed plasmid particles. The liposome-plasmid complexes had an average diameter of about 200 nm, as measured by dynamic light scattering.

C. Insertion of PEG

Distearol phosphatidylethanolamine (DSPE) was derivatized with PEG, as described by Zalipsky, 1992a. PEG-DSPE micelles were prepared from PEG-DSPE by dissolving 1 mM in water and sonicating.

Micelles of PEG-DTP-DSPE, that is, PEG attached to DSPE by a cleavable disulfide linkage (compound XV, prepared as described above in Example 2B), were prepared by dissolving 1 mM PEG-DTP-DSPE in water and sonicating.

Liposomes containing 2.5 mole percent of PEG-DSPE were prepared by adding 140 μl of the PEG-DSPE micelle suspension (1 μmole lipid/ml) to 5.6 μmoles lipid of the cationic lipid-plasmid complexes. The micelle-complex suspension was incubated for 5 minutes at room temperature with gentle vortexing to achieve insertion of the PEG-DSPE into the cationic liposomes (Uster, et al., 1996). This liposome formulation is indicted in FIGS. 6A–6B as "PEG".

Liposomes containing 1 mole percent of PEG-DSPE and 1 mole percent of PEG-DTP-DSPE were prepared as described above for the 2.5% PEG-DSPE liposomal composition, except the cationic liposome-plasmid complex was incubated with micelles of PEG-DSPE and PEG-DTP-DSPE to form liposomes having a surface coating of PEG chains, where half of the PEG chains were releasably attached to the liposome surface. This liposome formulation is indicted in FIGS. 6A–6B as "PEG+R-PEG".

Liposomes containing 2.5 mole percent of PEG-DTP-DSPE were prepared as described above, except the total amount of PEG included was PEG-DTP-DSPE. This liposome formulation is indicted in FIGS. 6A–6B as "R-PEG".

D. In Vivo Administration

The PEG-coated cationic liposome-plasmid complexes were administered to BALB/c mice obtained from Simonsen Laboratories (Gilroy, Calif.) by injection of about 100 nmoles lipid in 0.2–0.25 ml (approximately 100 µg plasmid) into the tail veins of 3 mice. 5 minutes after administration of the liposomes, 250 µl of 100 mM cysteine was injected via tail vein into each mouse. 24 hours after injection, the mice were sacrificed and tissues (lung, liver) were collected following perfusion with heparinized PBS (4° C.) under anesthesia.

At a temperature of between 0.4° C., 0.75 ml cell lysis reagent (Promega, Madison, Wis.) was added to each tissue, and the tissue was homogenized by 1 minute at 20,000 rpm. The supernatant was removed to a microcentrifuge tube and spun at 10,000 g for 5 minutes. The supernatant was collected for luciferase and protein assays. 20 µl of each sample was measured immediately, by a luminometer (100 µl of luciferin and ATP containing assay buffer, 10 second measurement). The relative light unit was normalized by the amount of protein in the extracts.

The results are shown in FIGS. 6A–6B.

Although the invention has been described with respect to particular embodiments, it will be apparent to those skilled in the art that various changes and modifications can be made without departing from the invention.

What is claimed is:

1. A method of administering an affinity moiety to a mammalian subject, comprising administering to the subject, liposomes with outer surfaces that contain (i) an affinity moiety effective to bind specifically to a target surface at which the therapy is aimed, and (ii) a hydrophilic polymer coating effective to shield the affinity moiety from interaction with the target surface, said hydrophilic polymer coating being made up of polymer chains which are covalently linked to surface lipid oomponents in the liposomes through releasable linkages, and allowing the administered liposomes to achieve a desired biodistribution, whereby said allowing is effective to cause release of a substantial portion of said linkages in the administered liposomes, thereby to expose the affinity moiety to the target surface.

2. The method of claim 1, wherein said releasable linkages are chemical linkages selected from the group consisting of disulfide, ester and peptide linkages.

3. The method of claim 2, wherein said releasable linkages are disulfide linkages.

4. The method of claim 1, wherein said hydrophilic polymer is selected from the group consisting of polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxyethylacrylate, hydroxymethylcellulose, hydroxyethylcellulose, polyethyleneglycol, and polyaspartamide.

5. The method of claim 1, wherein the hydrophilic polymer chains are polyethylene glycol chains having molecular weights in the range 500 to 10,000 daltons.

6. The method of claim 1, for administering a therapeutic agent to target cells, wherein the affinity moiety is a ligand effective to bind specifically with a cell-surface receptor on the target cells, and the liposomes further include the therapeutic agent in entrapped form.

7. The method of claim 6, for treatment of a solid tumor, wherein the affinity moiety is effective to bind specifically to a tumor-specific antigen, the liposomes have an average size between 30–400 nm.

8. The method of claim 6, for treatment at a site of inflammation, wherein the affinity moiety is effective to bind specifically to infected cells, the liposomes have an average size between 30–400 nm.

9. The method of claim 1, wherein the affinity moiety is a polypeptide or polysaccharide effector capable of inhibiting binding of a first binding member, which is a pathogen or cell in the bloodstream, to a second binding member, which is a target cell or cell matrix.

10. The method of claim 9, wherein the affinity moiety is selected from the group consisting of:

(a) a CD4 glycoprotein;

(b) a polysaccharide which binds to endothelial leukocyte adhesion molecule (ELAM);

(c) polymyxin B or polymyxin B decapeptide; and (d) a peptide.

11. The method of claim 1, wherein the liposomes further include such affinity moieties attached to distal ends of a portion of the hydrophilic polymer chains forming the hydrophilic polymer coating.

12. A liposome composition for use in treating a subject with an affinity moiety capable of inhibiting binding of a first binding member, which is a pathogen or cell in the bloodstream, to a second binding member, which is a target cell or cell matrix, comprising liposomes having outer surfaces that contain (i) a hydrophilic polymer coating composed of polyethylene glycol chains that are covalently linked to surface lipid components in the liposomes through releasable linkages, and (ii) said affinity moiety bound to the outer surfaces of said liposomes, such that the affinity moiety is shielded by said hydrophilic polymer coating from interaction with such binding members and is exposed for interaction with such binding members when at least a portion of the hydrophilic polymer coating is released.

13. The composition of claim 12, wherein said releasable linkages are chemical linkages selected from the group consisting of disulfide, ester and peptide.

14. The composition of claim 13, wherein said releasable linkages are disulfide linkages.

15. The composition of claim 12, wherein affinity moiety is selected from the group consisting of:

(a) a CD4 glycoprotein;

(b) a polysaccharide which binds to endothelial leukocyte adhesion molecule (ELAM);

(c) polymyxin B or polymyxin B decapeptide; and (d) a peptide.

* * * * *